(12) United States Patent
Mironov et al.

(10) Patent No.: US 10,206,430 B2
(45) Date of Patent: Feb. 19, 2019

(54) AEROSOL-GENERATING DEVICE, AND A CAPSULE FOR USE IN AN AEROSOL-GENERATING DEVICE

(71) Applicant: Philip Morris Products S.A., Neuchatel (CH)

(72) Inventors: Oleg Mironov, Neuchatel (CH); Michel Thorens, Moudon (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/108,967

(22) PCT Filed: Dec. 16, 2014

(86) PCT No.: PCT/EP2014/077920
§ 371 (c)(1),
(2) Date: Jun. 29, 2016

(87) PCT Pub. No.: WO2015/101479
PCT Pub. Date: Jul. 9, 2015

(65) Prior Publication Data
US 2016/0324215 A1 Nov. 10, 2016

(30) Foreign Application Priority Data
Dec. 31, 2013 (EP) .................................. 13199892

(51) Int. Cl.
*A24F 47/00* (2006.01)
*H05B 3/06* (2006.01)
(Continued)

(52) U.S. Cl.
CPC ............ *A24F 47/008* (2013.01); *A24B 15/16* (2013.01); *A61M 11/02* (2013.01); *A61M 11/08* (2013.01);
(Continued)

(58) Field of Classification Search
CPC .......... A24F 47/008; A24F 1/30; A24B 15/16; A24B 15/167; A61M 11/042; A24D 1/14; A24D 3/061
See application file for complete search history.

(56) References Cited

U.S. PATENT DOCUMENTS 4,692,590 A  9/1987 Spector
7,389,946 B2* 6/2008 Bruna ............... A61M 15/0028
222/327
(Continued)

FOREIGN PATENT DOCUMENTS

CN 101268867 A 9/2008
CN 102266125 A 12/2011
(Continued)

OTHER PUBLICATIONS

International Search Report and Written Opinion dated Mar. 13, 2015 in PCT/EP2014/077920 filed Dec. 16, 2014.
(Continued)

*Primary Examiner* — Edwin A. Leon
*Assistant Examiner* — Oscar Jimenez
(74) *Attorney, Agent, or Firm* — Oblon, McClelland, Maier & Neustadt, L.L.P.

(57) ABSTRACT

A capsule for an aerosol-generating device is provided, including a shell including a base and at least one side wall extending from the base, the shell containing an aerosol-forming substrate; and a lid sealed on the at least one side wall for forming a sealed capsule, wherein the base includes a recess extending into said shell along the longitudinal axis for receiving a heater of an aerosol-generating device. An aerosol-generating device is also provided, including a power supply; at least one heater; a cavity for receiving the capsule containing the aerosol-forming substrate; and a mouthpiece including a piercing element for piercing the lid of the capsule, wherein the at least one heater is configured
(Continued)

to be insertable into a recess of the capsule. An aerosol-generating system including the aerosol-generating device and the capsule is also provided.

12 Claims, 7 Drawing Sheets

(51) Int. Cl.
| | |
|---|---|
| *B29C 65/00* | (2006.01) |
| *B29C 65/48* | (2006.01) |
| *B29C 43/14* | (2006.01) |
| *A24B 15/16* | (2006.01) |
| *B65D 43/14* | (2006.01) |
| *A61M 15/00* | (2006.01) |
| *A61M 15/06* | (2006.01) |
| *A61M 13/00* | (2006.01) |
| *A61M 11/02* | (2006.01) |
| *A61M 11/08* | (2006.01) |
| *B29L 31/00* | (2006.01) |
| *B65D 83/14* | (2006.01) |

(52) U.S. Cl.
CPC ........ *A61M 13/00* (2013.01); *A61M 15/0011* (2014.02); *A61M 15/06* (2013.01); *B29C 43/14* (2013.01); *B29C 65/48* (2013.01); *B29C 66/53461* (2013.01); *B65D 43/14* (2013.01); *H05B 3/06* (2013.01); *A61M 15/0035* (2014.02); *A61M 2209/06* (2013.01); *B29L 2031/7174* (2013.01); *B29L 2031/7414* (2013.01); *B65D 83/14* (2013.01)

(56) References Cited

U.S. PATENT DOCUMENTS

| | | | |
|---|---|---|---|
| 9,445,630 B1* | 9/2016 | Modi | A24F 9/04 |
| 9,498,588 B2* | 11/2016 | Benassayag | A61M 15/06 |
| 9,603,389 B2* | 3/2017 | Chen | A24F 47/008 |
| 9,986,765 B2* | 6/2018 | Batista | A24F 47/008 |
| 2001/0032643 A1* | 10/2001 | Hochrainer | A61K 9/0078 |
| | | | 128/200.21 |
| 2009/0151717 A1* | 6/2009 | Bowen | A61M 11/041 |
| | | | 128/200.23 |
| 2009/0260642 A1 | 10/2009 | Monsees et al. | |
| 2010/0006113 A1 | 1/2010 | Urtsev et al. | |
| 2011/0220234 A1* | 9/2011 | Haas | A61M 15/0028 |
| | | | 138/109 |
| 2012/0111346 A1 | 5/2012 | Rinker et al. | |
| 2012/0111347 A1 | 5/2012 | Hon | |
| 2012/0204889 A1* | 8/2012 | Xiu | A24F 47/008 |
| | | | 131/273 |
| 2012/0279512 A1 | 11/2012 | Hon | |
| 2013/0037041 A1* | 2/2013 | Worm | A24F 47/008 |
| | | | 131/329 |
| 2013/0056013 A1* | 3/2013 | Terry | A24F 47/008 |
| | | | 131/328 |
| 2013/0068239 A1* | 3/2013 | Youn | A24F 47/008 |
| | | | 131/273 |
| 2013/0180533 A1* | 7/2013 | Kim | A24F 47/008 |
| | | | 131/273 |
| 2013/0228191 A1* | 9/2013 | Newton | A61M 15/06 |
| | | | 131/329 |
| 2013/0312776 A1* | 11/2013 | Newton | A61M 15/06 |
| | | | 131/329 |
| 2013/0319407 A1 | 12/2013 | Liu | |
| 2014/0041655 A1* | 2/2014 | Barron | A61M 11/042 |
| | | | 128/202.21 |
| 2014/0190477 A1 | 7/2014 | Qiu | |
| 2014/0305453 A1 | 10/2014 | Hon | |
| 2015/0034108 A1* | 2/2015 | Newton | A61M 15/06 |
| | | | 131/329 |
| 2015/0157056 A1* | 6/2015 | Bowen | A61M 11/041 |
| | | | 131/328 |
| 2015/0272225 A1* | 10/2015 | Worm | A24F 47/008 |
| | | | 131/328 |
| 2016/0235122 A1* | 8/2016 | Krietzman | A24F 47/008 |
| 2017/0035113 A1* | 2/2017 | Thorens | A24F 47/008 |
| 2017/0035116 A1* | 2/2017 | Batista | A24F 47/008 |
| 2017/0071251 A1* | 3/2017 | Goch | A24F 47/008 |
| 2017/0079331 A1* | 3/2017 | Monsees | A61M 15/06 |
| 2017/0172203 A1* | 6/2017 | Gebara | A24F 1/30 |

FOREIGN PATENT DOCUMENTS

| | | |
|---|---|---|
| CN | 103202538 A | 7/2013 |
| DE | 10 2012 100 831 B3 | 2/2013 |
| EP | 2404515 A1 | 1/2012 |
| EP | 2617303 A1 | 7/2013 |
| JP | 2014-217379 | 11/2014 |
| WO | WO97/46293 a1 | 12/1997 |
| WO | WO 2007/012007 A2 | 1/2007 |
| WO | WO 2009/079641 A2 | 6/2009 |

OTHER PUBLICATIONS

Decision of Grant with English translation dated Nov. 1, 2018 in corresponding Japanese Patent Application No. 2016-544100, (6 pages).
Chinese Office Action dated Dec. 3, 2018 in corresponding Chinese Patent Application No. 201480067075.X, (6 pages).

* cited by examiner

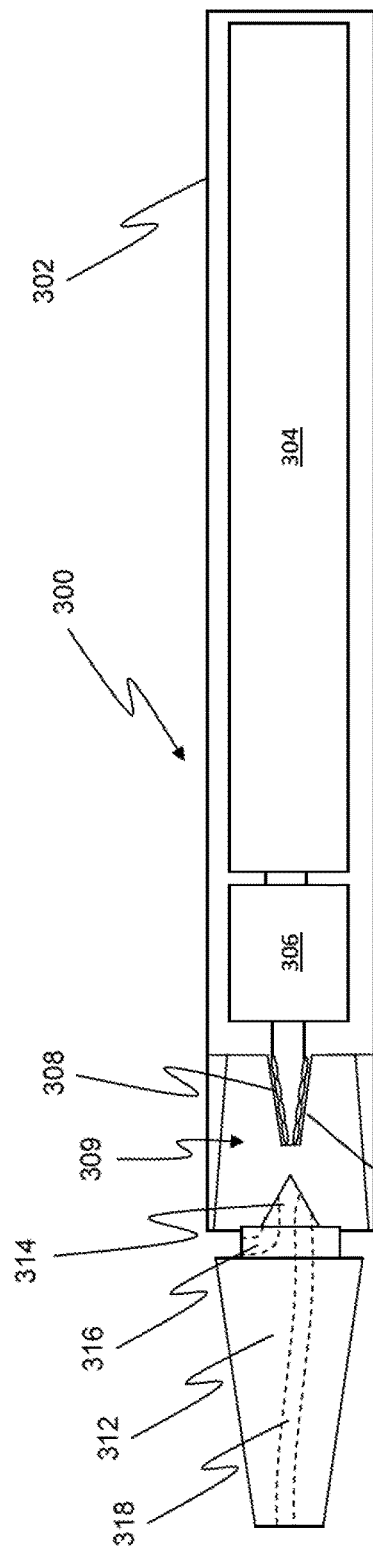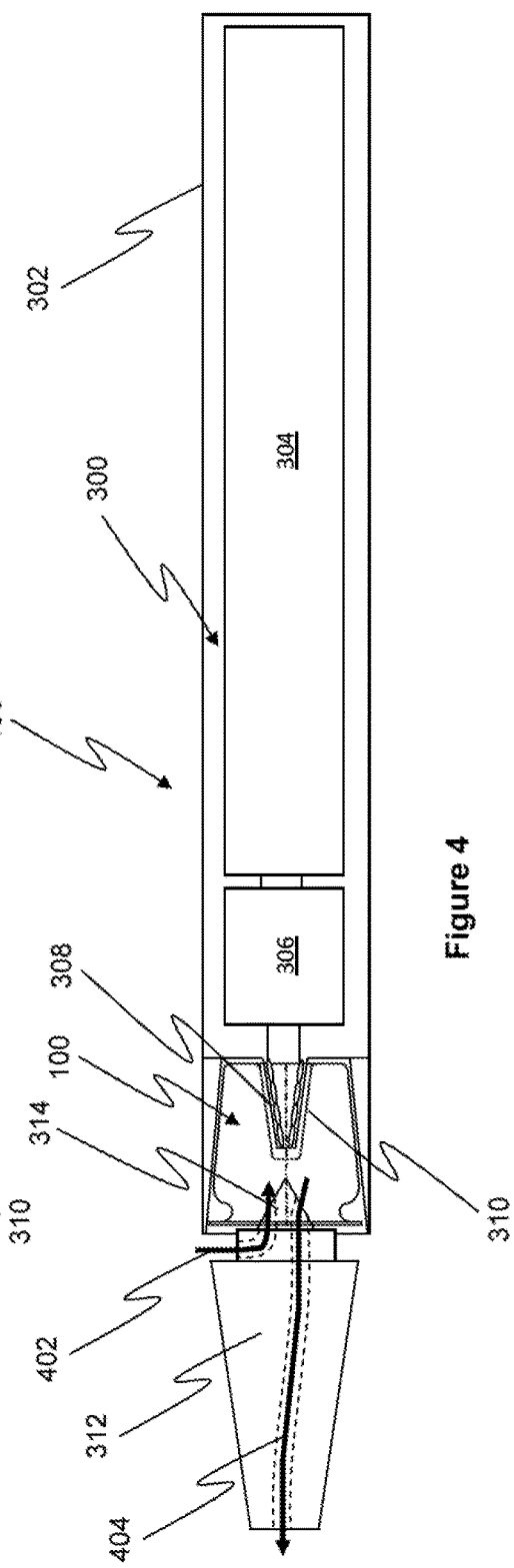

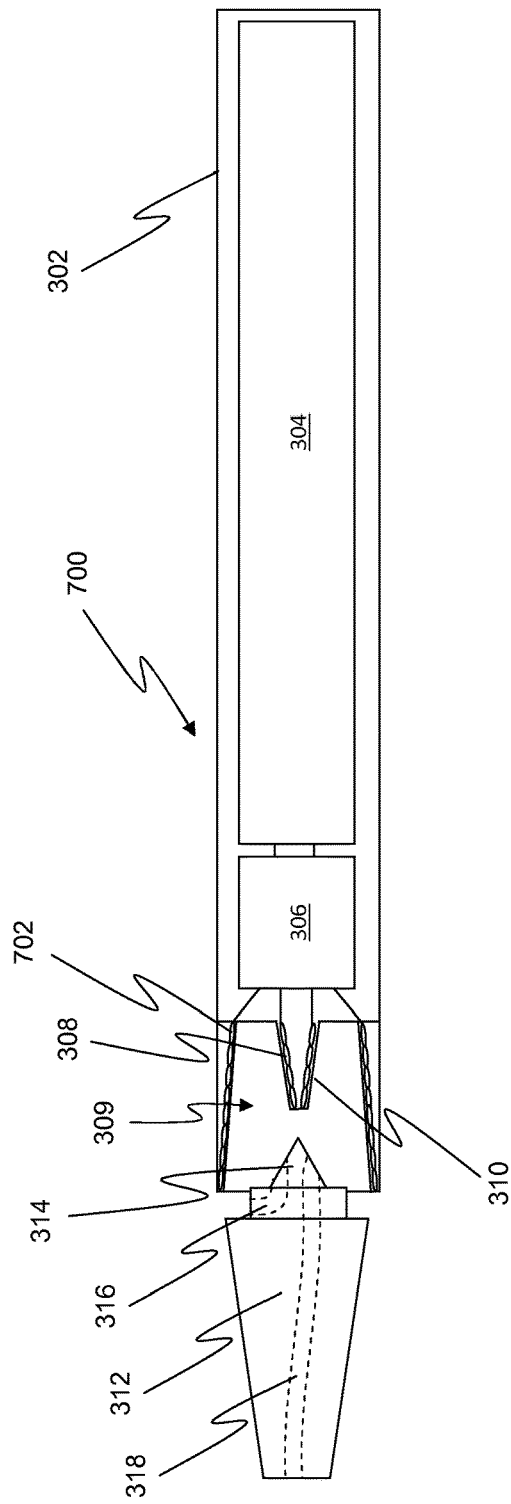

AEROSOL-GENERATING DEVICE, AND A CAPSULE FOR USE IN AN AEROSOL-GENERATING DEVICE

The present invention relates to a capsule for an aerosol-generating device, and an aerosol-generating device and system. In particular, the invention relates to an electrically operated aerosol-generating device, such as an electrically heated device.

Aerosol-generating systems comprising capsules and an aerosol-generating devices are known. One particular system is disclosed in WO 2009/079641, and comprises a capsule comprising a shell containing viscous vaporisable material and an aerosol-former, such as propylene glycol. The shell is sealed by a lid which can be penetrated by the aerosol-generating device when the capsule is inserted therein to allow airflow through the capsule when in use. The device comprises a heater configured to heat the external surface of the shell to a temperature up to about 200 degrees C., and in one example the external surface of the shell is heated to 170 degrees C. The aerosol-generating device is elongate and has a diameter similar to that of a conventional combustible smoking article (a cigarette) and as such the heater is necessarily very close to the external wall of the device. It has been found that the proximity of the heater to the external wall of the device results in an external temperature of the device housing in the region of the heater of over 90 degrees. At the very least, this can be uncomfortable for the user. In addition, the time to first puff of the device has been found to be up to 30 seconds.

As can be seen, the known capsule heating aerosol-generating systems presents a number of problems. It is therefore an object of the present invention to ameliorate those problems and provide a capsule for an aerosol-generating device and an aerosol-generating device that improves the efficiency of the heater, enables a reduction in the external wall temperature of the device, and reduces the time to first puff.

According to an aspect of the present invention, there is provided a capsule for an aerosol-generating device. The capsule comprises: a shell comprising a base and at least one side wall extending from the base, the shell containing an aerosol-forming substrate, having a solid or liquid component, or both solid and liquid components; and a lid sealed on the at least one side wall for forming a sealed capsule. The base comprises a recess extending into the shell along the longitudinal axis for receiving a heater of an aerosol-generating device.

As will now be appreciated by one of ordinary skill in the art, providing a recess in the base of the capsule, advantageously, reduces the maximum distance from the heater to aerosol-forming substrate, reducing the power requirements, and reducing the maximum temperature required at the heater to provide a minimum temperature to all of the aerosol-forming substrate. As will be appreciated, the incorporation of the recess increases the ratio of the surface area to the volume of the aerosol-forming substrate. Thus, the maximum thickness of the aerosol-forming substrate is reduced.

Conversely, this enables a higher operating temperature, and so aerosol-formers having a higher boiling point can be used which improves the user experience as the aerosol droplet size will likely be smaller.

In addition, moving the heater to within a recess in the capsule, as compared to the external heaters of the known systems, enables a decrease in the external temperature of the aerosol-generating device improving the user experience, while also enabling an increase in the operating temperature.

As used herein, the term "longitudinal" refers to the direction between the proximal, or lid, end and opposed distal, or base, end of the capsule, and refers to the direction between the proximal, or mouthpiece, end and the distal end of the aerosol-generating device.

The aerosol-forming substrate is preferably a substrate capable of releasing volatile compounds that can form an aerosol. The volatile compounds are released by heating the aerosol-forming substrate.

The aerosol-forming substrate may be solid or liquid or comprise both solid and liquid components. In a preferred embodiment, the aerosol-forming substrate is solid.

The aerosol-forming substrate may comprise nicotine. The nicotine containing aerosol-forming substrate may be a nicotine salt matrix. The aerosol-forming substrate may comprise plant-based material. The aerosol-forming substrate may comprise tobacco, and preferably the tobacco containing material contains volatile tobacco flavour compounds, which are released from the aerosol-forming substrate upon heating. The aerosol-forming substrate may comprise homogenised tobacco material.

Homogenised tobacco material may be formed by agglomerating particulate tobacco. Where present, the homogenised tobacco material may have an aerosol-former content of equal to or greater than 5% on a dry weight basis, and preferably between greater than 5% and 30% by weight on a dry weight basis.

The aerosol-forming substrate may alternatively comprise a non-tobacco-containing material. The aerosol-forming substrate may comprise homogenised plant-based material.

The aerosol-forming substrate may comprise at least one aerosol-former. The aerosol-former may be any suitable known compound or mixture of compounds that, in use, facilitates formation of a dense and stable aerosol and that is substantially resistant to thermal degradation at the operating temperature of the aerosol-generating device. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Particularly preferred aerosol formers are polyhydric alcohols or mixtures thereof, such as triethylene glycol, 1,3-butanediol and, most preferred, glycerine.

The aerosol-forming substrate may comprise other additives and ingredients, such as flavourants.

The aerosol-forming substrate preferably comprises nicotine and at least one aerosol-former. In a particularly preferred embodiment, the aerosol-former is glycerine. The improved efficiency, reduced maximum distance from the heater to the aerosol-forming substrate, and insulation properties of providing enabling the heater to be internal to the capsule enables a higher operating temperature. The higher operating temperature enables glycerine to be used as an aerosol-former which provides an improved aerosol as compared to the aerosol-formers used in the known systems.

To enable the maximum distance of the heater to the aerosol-forming substrate to be further reduced, the longitudinal length of the recess is preferably at least about 50% of the longitudinal length of the at least one side wall. The longitudinal length of the recess may be between about 50% and about 75% of the longitudinal length of the at least one side wall.

The base of the shell is preferably substantially circular, and the recess preferably has a substantially circular cross-section. In this embodiment, the ratio of the radius of the base to the radius of the recess in the base is between about 1.5 and about 4.0. By providing the recess with a circular cross-section having such a radius advantageously reduces the maximum distance from the heater to aerosol-forming substrate while providing sufficient volume within the capsule to contain enough aerosol-forming substrate to provide the user with a good user experience.

The radius of the base of the capsule is preferably between about 3 mm and about 6 mm, more preferably between about 4 mm and about 5 mm, and in a particularly preferred embodiment the radius of the base is about 4.5 mm. In this particularly preferred embodiment, the radius of the recess is between about 1.5 mm and about 3 mm.

The recess preferably has a frusto-conical shape, and a substantially circular cross-section. Providing a recess with a frusto-conical shape advantageously enables the capsule to be located, and positioned correctly, within an aerosol-generating device more easily, and enables the shell to be manufactured more easily.

The frusto-conical shape may be angled away from 90 degrees by between about 5 degrees and about 20 degrees, more preferably between about 7.5 degrees and about 12.5 degrees.

The longitudinal length of the at least one side wall is preferably at least 2 times the radius of the base. Advantageously, a shell having such dimensions may further reduce the maximum distance of the heater to the aerosol-forming substrate. Again, having such an aspect ratio enables the maximum thickness of the aerosol-forming substrate to be reduced while providing sufficient volume within the capsule to contain enough aerosol-forming substrate to provide the user with a good user experience.

The longitudinal length of the capsule is preferably between about 7 mm and about 13 mm, more preferably between about 9 mm and about 11 mm, and in a particularly preferred embodiment the longitudinal length of the capsule is about 10.2 mm. In this particularly preferred embodiment, the longitudinal length of the recess is between about 5 mm and about 7.5 mm.

The shell preferably has a wall thickness of between about 0.1 mm and about 0.5 mm, more preferably between about 0.2 mm and about 0.4 mm, and in a particularly preferred embodiment, the wall thickness of the shell is about 0.3 mm. Providing a thin walled shell reduces the thermal mass of the shell that is required to be heated, and thus the time require to heat the capsule to the operating temperature may be reduced.

The wall thickness of the recess may be the same as the wall thickness of the shell. Alternatively, the wall thickness of the recess may be less than the wall thickness of the shell. Providing the recess with a wall thickness less than that of the shell may yet further reduce the time require to heat the capsule to the operating temperature, while maintaining the structural rigidity of the capsule.

The shell, base and recess are preferably integrally formed. The material used to form the shell, base and recess may be metal, preferably aluminium. Alternatively, the material used to form the shell, base and recess may be polymeric, such as any suitable polymer capable of withstanding the operating temperature of the aerosol-forming device.

The lid is preferably made from a polymer, or a metal, and more preferably is made from aluminium. The lid may be laminated to improve the sealing ability, and in a particularly preferred embodiment is laminated, food grade, anodised aluminium.

The capsule is preferably filled with sufficient aerosol-forming substrate to reach a level between about 75% and about 150% of the longitudinal length of the recess, more preferably between about 90% and about 110% of the longitudinal length of the recess. By filling the capsule with such an a level of aerosol-forming substrate, the maximum distance from the heater to the aerosol-forming substrate can be minimised.

The aerosol-forming substrate may be coated on the walls of the shell and recess, and may not completely fill the volume of the shell. By coating the aerosol-forming substrate on the walls of the shell and recess the maximum thickness of the aerosol-forming substrate may be reduced. In addition, coating the aerosol-forming substrate in this way may improve the airflow within the capsule thus improving the entrainment of the aerosol into the airflow.

The capsule is preferably filled with between about 150 mg and about 400 mg of aerosol-forming substrate, more preferably between about 200 mg and about 300 mg of aerosol-forming substrate, and in a preferred embodiment about 250 mg of aerosol-forming substrate.

As described above, the aerosol-forming substrate may be liquid. In such embodiments, the capsule is provided with a high liquid retention material to substantially prevent leakage of the liquid aerosol-forming substrate from the capsule when in use. The high liquid retention material may be a sponge-like material.

The capsule may be manufactured using any suitable method. In a preferred embodiment, the shell is manufactured using a deep drawing process. The aerosol-forming substrate may then be sprayed within the shell, or filled using any other suitable means. The shell is then sealed with the lid. The lid may be sealed to the shell of the capsule using any suitable method, including: adhesive, such as an epoxy adhesive; heat sealing; ultrasonic welding; and laser welding.

According to a further aspect of the present invention, there is provided an aerosol-generating device. The device comprises: power supply; at least one heater; a cavity for receiving a capsule containing an aerosol-forming substrate as described herein; and a mouthpiece comprising a piercing element for piercing the lid of a capsule. The at least one heater is configured to be insertable into the recess of a capsule.

Providing a heater configured to be insertable into the recess of a capsule advantageously reduces the maximum temperature required of the heater because the aerosol-forming substrate in the capsule is on average closer to the heater. As a consequence the time to first puff is reduced. In addition, the insulating effect of the aerosol-forming substrate, and the various other components and layers of material between the heater and the outer surface of the device advantageously reduces the external temperature of the device.

The shape and dimensions of the external surface of the at least one heater are preferably configured to substantially match the shape and dimensions of the recess of a capsule. By matching the shape and dimensions the heat transfer from the heater to the capsule may be improved. As such, the at least one heater is preferably frusto-conical to match the preferably shape of the recess in a capsule.

The dimensions of the frusto-conical shaped heater are preferably as follows. The radius of the base of the frusto-conical shape is preferably between about 1.5 mm and about 3 mm.

The frusto-conical shape of the heater may be angled away from 90 degrees by between about 5 degrees and about 20 degrees, more preferably between about 7.5 degrees and about 12.5 degrees.

The longitudinal length of the heater is preferably between about 5 mm and about 7.5 mm.

The at least one heater is preferably provided within a heater housing, the heater housing being a thin-walled frusto-conical shape. The heater housing provides protection for the at least one heater during use and in particular during insertion of a capsule. The heater housing is also adapted to align the capsule within the aerosol-forming device. The at least one heater is preferably affixed within the heater housing using an epoxy compound. Preferably the heater housing is filled with the epoxy compound, and that it to say the heater is potted within the heater housing. The epoxy compound is preferably suitable for transferring heat efficiently from the heater to the capsule.

The cavity for receiving a capsule is configured to substantially match the shape and dimensions of a capsule. The cavity walls may be insulated. The insulation may reduce the external wall temperature of the device.

The aerosol-generating device may comprise at least two heaters consisting of: at least one first internal heater configured to be insertable in the recess of a capsule; and, at least one second external heater within the interior of the cavity. Alternatively, the second external heater may be provided such that it surrounds the cavity for receiving the capsule. In this embodiment, the at least one second heater preferably conforms to the shape of side walls of the cavity. Conforming the heater to the shape of the cavity improves the heat transfer from the second heater to the capsule. Regardless of the position of second heater, a further reduction in time to first puff may be achieved by providing a second heater.

The at least one second external heater may surround the cavity, and may be adjacent the external wall of the cavity. In this embodiment, the heater is affixed to the cavity wall using an epoxy compound. The epoxy compound is preferably suitable for transferring heat efficiently from the heater to the capsule.

The or each heater is preferably an electrically powered heater comprising at least one electrically resistive track provided on a flexible substrate. By providing a heater comprising electrically resistive tracks on a flexible substrate, the heater may be easier to manufacture and form into the required shape to conform to the recess of a capsule. The electrically resistive track may be any one of: platinum; gold; and silver or any other resistive material that may provide a sufficiently high temperature when provided with an electrical current during operation such that a sufficiently dense aerosol is formed.

The power supply may be a battery, and may be a rechargable battery configured for many cycles of charge and discharge. The battery may be a Lithium based battery, for example a Lithium-Cobalt, a Lithium-Iron-Phosphate, a Lithium Titanate or a Lithium-Polymer battery. The battery may alternatively be a Nickel-metal hydride battery or a Nickel cadmium battery. The battery capacity is preferably selected to allow for multiple uses by the user before requiring recharging. The capacity of the battery is preferably sufficient for a minimum of 20 uses by the user before recharging is required.

The mouthpiece of the aerosol-generating device preferably comprises at least one air inlet and at least one air outlet, and the piercing element comprises at least one first conduit extending between the at least one air inlet and a distal end of the piercing element. The mouthpiece preferably further comprises at least one second conduit extending between a distal end of the piercing element and the at least one air outlet. The mouthpiece is therefore preferably arranged, such that, in use, when a user draws on the mouthpiece, air flows along an airflow pathway extending from the at least one air inlet, through the at least one first conduit, through a portion of the capsule, through the at least one second conduit and exits the at least one outlet. Providing such conduits enables improved airflow through the device and enables the aerosol to be delivered to the user more easily.

The aerosol-generating device preferably further comprises control electronics. The control electronics are preferably configured to supply power from the power supply to the at least one heater. The control electronics are preferably further configured to maintain the temperature of the at least one heater at an operating temperature of between about 100 degrees C. to 260 degrees C., more preferably 180 degrees C. and about 260 degrees C., and most preferably between about 220 degrees C. and about 240 degrees C.

The aerosol-generating device may further comprise a temperature sensor adjacent the cavity for receiving the capsule. The temperature sensor is in communication with the control electronics to enable the control electronics to maintain the temperature at the operating temperature. The temperature sensor may be a thermocouple, or alternatively the at least one heater may be used to provide information relating to the temperature. In this alternative, the temperature dependent resistive properties of the at least one heater are known, and are used to determine the temperature of the at least one heater in a manner known to the skilled person.

The aerosol-generating device may comprise a puff detector in communication with the control electronics. The puff detector is preferably configured to detect when a user draws on the aerosol-generating device mouthpiece. The control electronics are preferably further configured to control power to the at least one heating element in dependence on the input from the puff detector.

The aerosol-generating device further comprises a housing comprising the cavity and other components. The housing of the aerosol-generating device is preferably elongate, such as an elongate cylinder having a circular cross-section.

The aerosol-generating device preferably further comprises a user input, such as a switch or button. This enables the user to turn the device on. The switch or button may initiate the aerosol generation or prepare the control electronics to await input from the puff detector.

In use, the user inserts a capsule as described herein into the cavity of an aerosol-generating device as described herein. The user then attaches the mouthpiece to the main body of the aerosol-generating device which pierces the capsule with the piercing portion. The user then activates the device by pressing the button. The user then draws on the mouthpiece which draws air into the device through the air inlet, the air then passes through the capsule entraining the vapourised aerosol-forming substrate into the airflow, and the exits the device through the air outlet in the mouthpiece to be inhaled by the user.

According to a yet further aspect of the present invention there is provided an aerosol-generating system comprising an aerosol-generating device as described herein and a capsule as described herein.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention will be further described, by way of example only, with reference to the accompanying drawings in which:

FIG. 3 shows a cross-sectional view of an aerosol-generating device according to the present invention;

FIG. 4 shows a cross-sectional view of an aerosol-generating system according to the present invention;

FIG. 7 shows a cross-sectional view of an alternative aerosol-generating device according to the present invention.

Figure 1A:
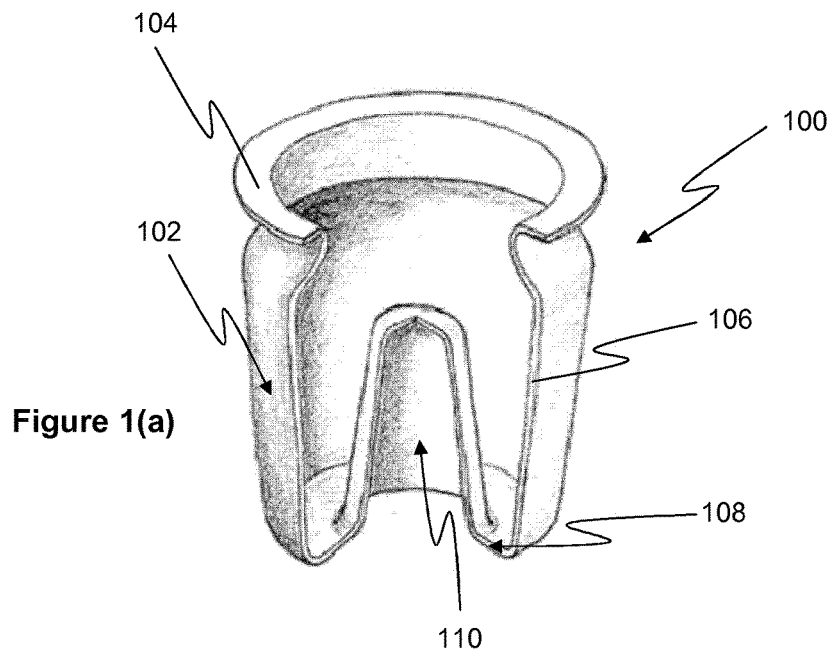
FIG. 1 shows a cut-away isometric view of a capsule according to the present invention.

FIG. 1(a) shows a cut-away isometric view of a capsule 100 for use in an aerosol-generating device. The capsule comprises a shell 102 containing an aerosol-forming substrate (not shown), the shell is sealed by a lid (not shown) which is sealed to the lip portion 104.

The shell 102 of the capsule 100 comprises a thin-walled external side wall 106 and a thin-walled base 108. The base 108 comprises a recess 110 positioned centrally therein. The recess is frusto-conical in shape and is configured to receive a heater when the capsule is inserted into an aerosol-generating device.

The shell of the capsule is formed using deep drawing in at least two stages. Stage 1 comprises deep drawing the shell and recess using a suitable die and punch. It will be appreciated by one of ordinary skill in the art that the shell and recess may alternatively be formed in two stages. The lip of the shell is then formed in the stage 2 of the process. The manufacturing process is described below in further detail with reference to FIG. 6.

Figure 1B:
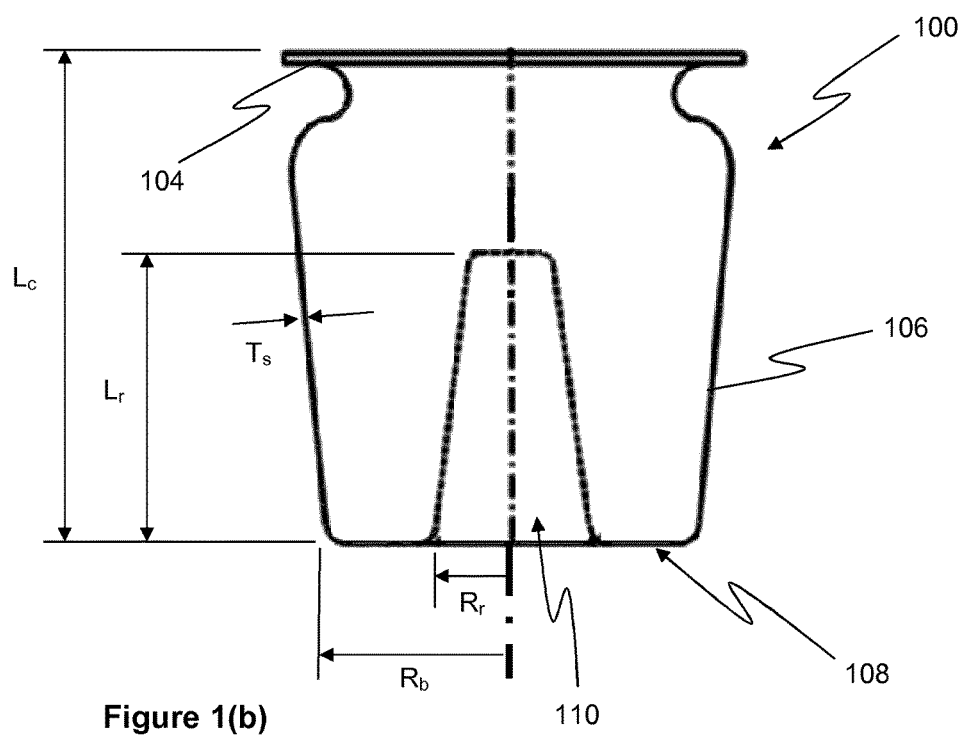

FIG. 1(b) shows a cross-sectional view of the capsule 100. The capsule 100 has longitudinal length $L_c$, and the base of the capsule has a radius $R_b$. The external side wall 106 of the shell has a thickness $T_s$. The recess 110 in the base 108 of the shell has a longitudinal length $L_r$, and the radius of the recess 110 at the base is $R_r$.

The base of the capsule is approximately 4.5 mm in radius ($R_b$), and the longitudinal length of the capsule is approximately 10.2 mm ($L_c$). The walls of the capsule are approximately 0.3 mm in thickness ($T_s$).

Figure 2:
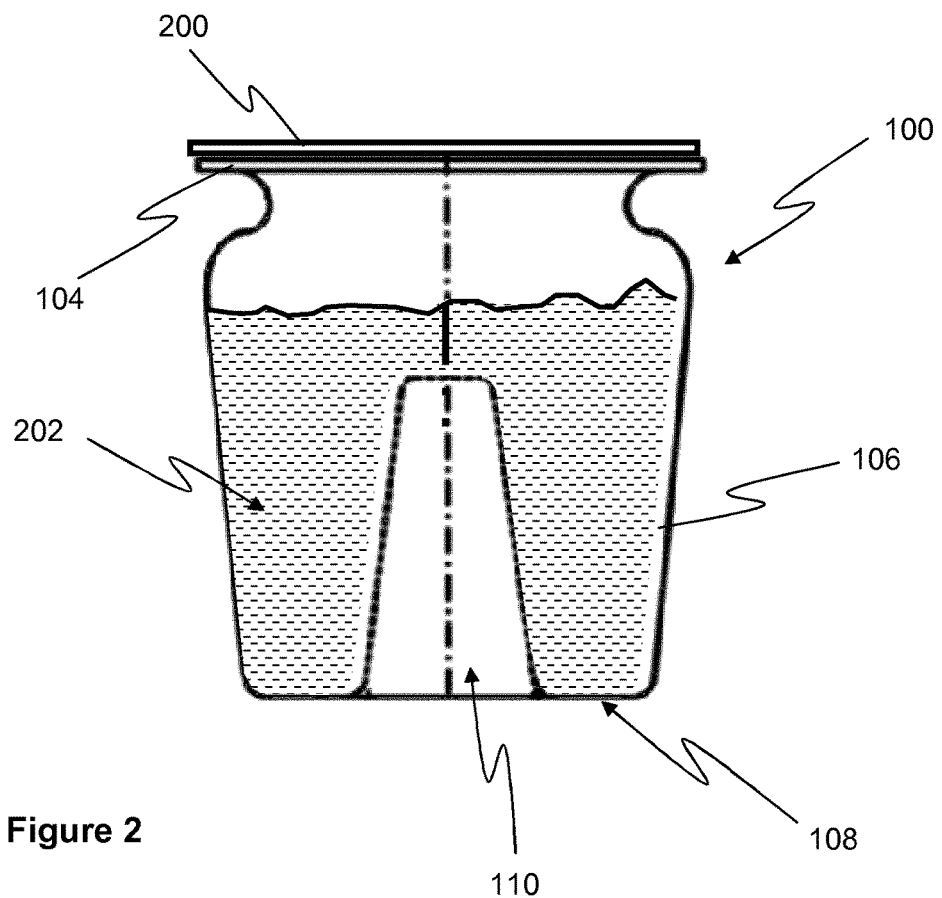
FIG. 2 shows a cross-sectional view of a capsule according to the present invention.

FIG. 2 shows a cross-sectional view of the capsule 100 for use in an aerosol-generating device. As can be seen, and as described above, the lid 200 is sealed to the lip portion 104. The lid may be sealed using any suitable method, including: adhesive, such as an epoxy adhesive, heat sealing, ultrasonic welding, or laser welding. Before the lid is sealed to the lip portion, the shell 102 of the capsule is filled with an aerosol-forming substrate 202. Approximately 250 mg of aerosol-forming substrate is provided within the shell. The aerosol-forming substrate comprises a nicotine containing material, such as tobacco, and an aerosol-former. The aerosol-former is glycerine that provides a good mouth feel for the user; it has also been found that glycerine produces a suitably small aerosol droplet diameter as compared to other aerosol-formers.

FIG. 3 shows a cross-sectional view of an aerosol-generating device 300 for use with a capsule 100 as described above. The aerosol-generating device comprises an outer housing 302, adapted to house: a power supply 304 such as a rechargeable battery; control circuitry 306; and an electrical heater 308. The housing 302 further comprises a cavity 309 configured to receive a capsule 100. The electrical heater is housed within a heater housing 310 having a frusto-conical shape configured to match the frusto-conical shape of the recess of a capsule. The aerosol-generating device 300 further comprises a mouthpiece 312 attachable to a proximal end of the aerosol-generating device housing 302. The mouthpiece comprises a piercing portion 314, and two airflow conduits, a first or inlet conduit 316 and a second or outlet conduit 318.

FIG. 4 shows a cross-sectional view of an aerosol-generating system 400 comprising an aerosol-generating device 300 and a capsule 100 as described above; like reference numerals refer to like components. The capsule is received in the cavity of the housing and the heater is inserted within the recess of the capsule.

In use, the user inserts the capsule 100 into the cavity of the aerosol-generating device 300, and then attaches the mouthpiece 312 to the housing 302. By attaching the mouthpiece, the piercing portion 314 pierces the lid of the capsule, and forms an airflow pathway from the air inlet, through the capsule to the air outlet. FIG. 4 shows the portion of the airflow pathway entering the capsule 402, and the portion of the airflow pathway 404 exiting the capsule. The user then presses a button (not shown) to activate the device. In activating the device, the heater is supplied with power by the control electronics 306 from the power supply 304. When the temperature of the capsule reaches the operating temperature of between about 220 degrees C. and about 240 degrees, the user is informed by means of an indicator (not shown) that the user may then draw on the mouthpiece. When the user draws on the mouthpiece, air enters the air inlet, proceeds through the conduit 316 within the mouthpiece and into the capsule, entrains vapourised aerosol-forming substrate, and then exits the capsule via the outlet conduit 318 in the mouthpiece.

Figure 5A:
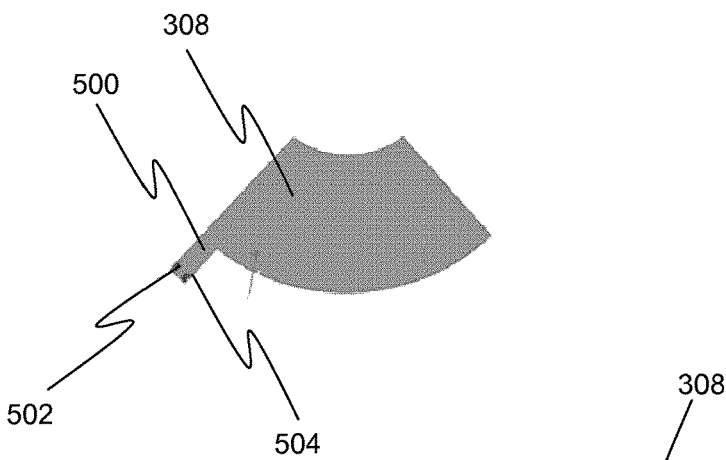
FIG. 5 show schematic diagrams of an electrically resistive heater for an aerosol-generating device according to the present invention.

FIG. 5(a) shows the electrical heater 308 for the aerosol-generating device as described above. The electrical heater comprises a flexible polymeric substrate having an electrically resistive material, such as platinum, gold or silver, printed thereon in tracks (not shown). The heater 308 is provided with a tab 500 comprising electrical contacts 502 and 504 for connection to the power supply 304 via the control circuitry 306.

Figure 5B:
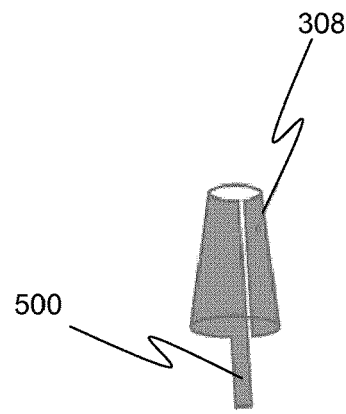
Figure 5C:
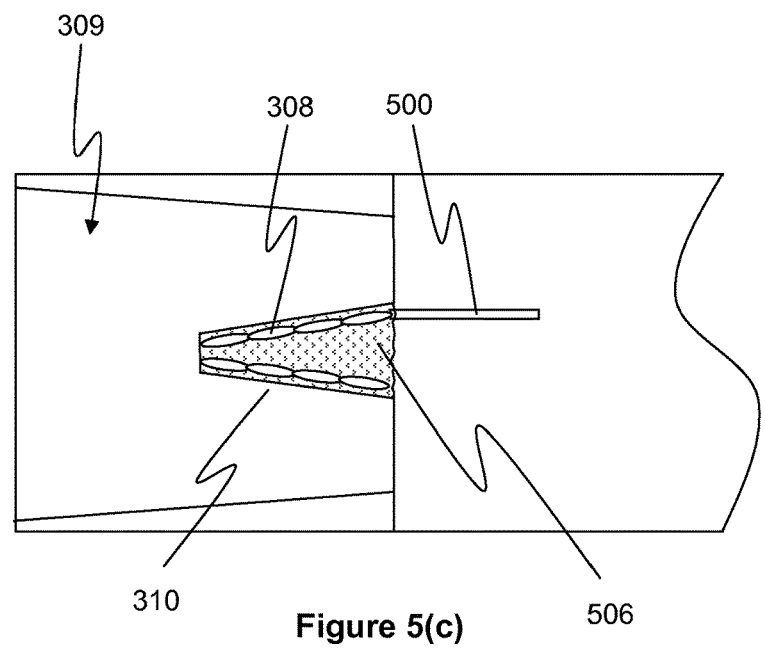

FIG. 5(b) shows the electrical heater 308 formed into the frusto-conical shape as used in the aerosol-generating device 300. The heater is formed into the frusto-conical shape by rolling the flexible substrate. As shown in FIG. 5(c), the formed heater is then inserted into the heater housing 310, and potted into the housing by filling the housing with an epoxy compound 506 to retain the heater in place.

As described above, the shell 102 of the capsule may be manufactured in a two-stage process, the shell 102 is then filled with the aerosol-forming substrate 202, and then sealed with lid 200 to form the capsule. The process will now be described in detail with reference to FIG. 6.

Figures 6A, 6B, 6C, 6D, 6E, 6F:
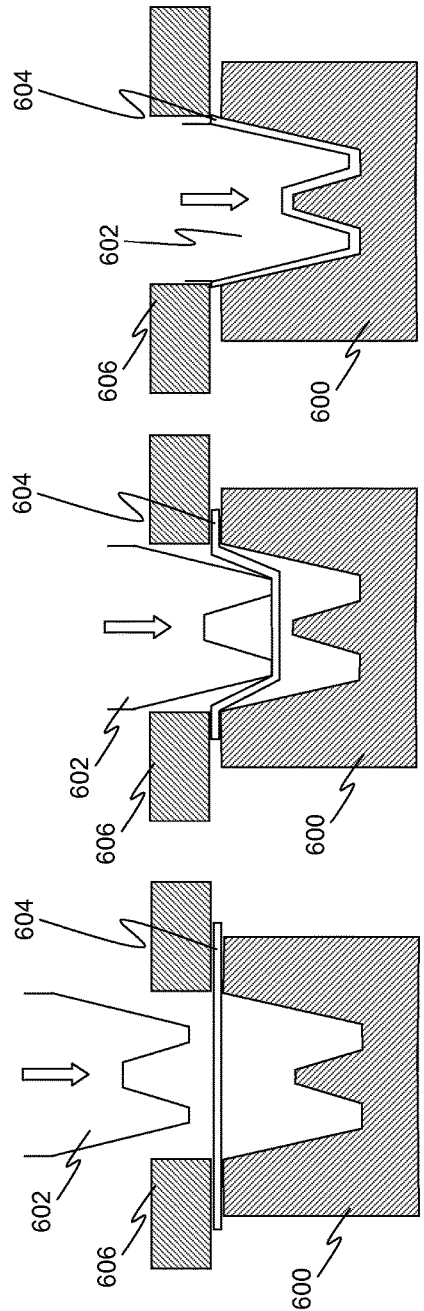
FIG. 6 show a manufacturing process of a capsule according to the present invention.

The first stage of the process to form the shell is shown in FIGS. 6(a). 6(b) and 6(c). A die 600, having the required form of the shell, and a corresponding punch 602 is provided. A blank 604 which is substantially circular in shape is slidably clamped to the die by the clamp 606. The clamp 606 enables the blank 604 to slide along the top surface of the die 600 as it is drawn into the die 600 by the punch 602. It will be appreciated by one of ordinary skill that this process may involve a number of intermediate stages having multiple dies and punches to slowly reduce the size of the formed blank to the final required size.

Once the first stage is complete, the second stage of the manufacturing process forms the lip 104 of the shell to enable the lid to be sealed to the shell. FIGS. 6(d) and 6(e) show this second stage of the process. The two-part die 608 and 610 is advanced onto the partially formed blank 604 to partially form the neck of the lip 104. To aid the forming process, the two-part die, or alternatively the blank, may be rotated about the longitudinal axis as the two-part die is advanced onto the blank. In FIG. 6(e) it can be seen that a further die is used to finally form the lip 104. The die is advanced onto the partially formed blank to bend the blank material into the lip. Again, the die, or the partially formed blank, may be rotated about the longitudinal axis to aid in the forming process.

FIG. 6(f) shows the now formed shell 102 being filled with aerosol-forming substrate 202 by the spray gun 614. FIG. 6(g) shows the filled shell.

Figure 6I:
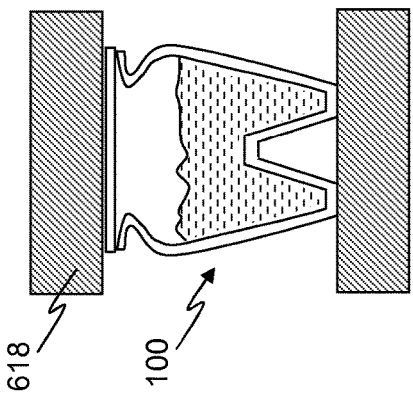
Figure 6H:
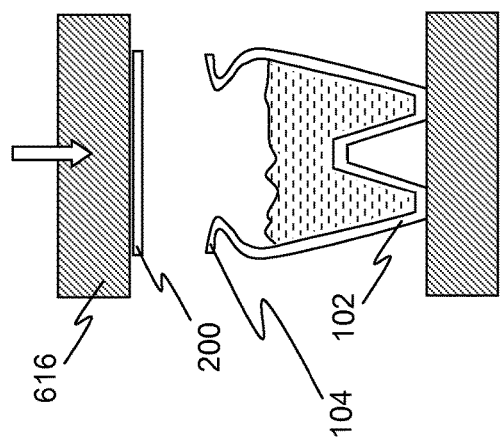
Figure 6G:
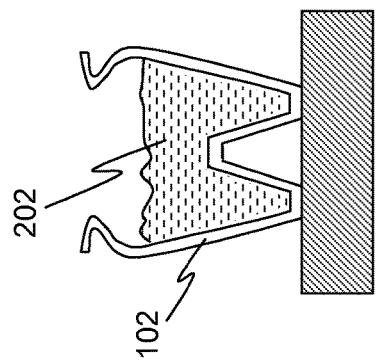

FIGS. 6(h) and 6(i) show the final process of sealing the lid 200 to the shell 102. The lid 200 is advanced towards the shell 102 by the lid holder 616. The lid holder may be a vacuum holder or any other suitable holder as will be appreciated by one of ordinary skill in the art. The lid may be provided with glue or any other suitable sealing means. Finally, the lid 200 is sealed to the shell 102. In this example, the lid is heat sealed to the shell by the heater 618 which melts the adhesive pre-applied to the lid.

As will be appreciated to one of ordinary skill in the art, the aerosol-generating device shown in FIG. 3 is only one example of aerosol-generating devices according to the present invention. One other such example is shown in FIG. 7. The aerosol-generating device 700 shown in FIG. 7 is similar to that shown in FIG. 3, and like reference numerals refer to like features.

The aerosol-generating device comprises an outer housing 302, adapted to house: a power supply 304 such as a rechargeable battery; control circuitry 306; an internal electrical heater 308; and an external electrical heater 702. The housing 302 further comprises a cavity 309 configured to receive a capsule 100. The internal electrical heater 308 is housed within a heater housing 310 having a frusto-conical shape configured to match the frusto-conical shape of the recess of a capsule. The external heater 702 is provided within the cavity 309. The aerosol-generating device 300 further comprises a mouthpiece 312 attachable to a proximal end of the aerosol-generating device housing 302. The mouthpiece comprises a piercing portion 314, and two airflow conduits, a first or inlet conduit 316 and a second or outlet conduit 318.

In use, the aerosol-generating device 700 operates in the same way as that aerosol-generating device 300 as described above with reference to FIG. 4. However, the control circuitry 306 provides power to both the internal heater 308 and the external heater 702. The additional external heater 702 provides further heating to the capsule to, for example, further decrease the time to first puff and to improve the heat transfer to the aerosol-forming substrate by yet further reducing the maximum distance from a heater the aerosol-forming substrate.

The invention claimed is:

1. An aerosol-generating system, comprising:
   a capsule comprising:
      a shell comprising a base and at least one side wall extending from the base, the shell containing an aerosol-forming substrate having a solid component and comprising at least one of a nicotine salt matrix and tobacco, and
      a lid sealed on the at least one side wall for forming a sealed capsule,
      wherein the base comprises a recess extending into said shell along a longitudinal axis of the capsule; and
   an aerosol-generating device comprising:
      a power supply,
      at least one heater,
      a cavity configured to receive the capsule, and
      a mouthpiece comprising a piercing element configured to pierce the lid of the capsule,
      wherein the at least one heater is configured to be insertable into the recess of the capsule, and
      wherein the mouthpiece comprises at least one air inlet and at least one air outlet, and the piercing element comprises at least one first conduit extending between the at least one air inlet and a distal end of the piercing element, and at least one second conduit extending between the distal end of the piercing element and the at least one air outlet, such that in use, when a user draws on the mouthpiece, air flows along an airflow pathway extending from the at least one air inlet, through the at least one first conduit, through a portion of the capsule, through the at least one second conduit, and exits the at least one outlet.

2. The aerosol-generating system according to claim 1, wherein a shape and dimensions of an external surface of the at least one heater are configured to substantially match a shape and dimensions of the recess of the capsule.

3. The aerosol-generating system according to claim 1, wherein the at least one heater is frusto-conical.

4. The aerosol-generating system according to claim 1, comprising at least two heaters consisting of at least one first heater configured to be insertable in the recess of the capsule and at least one second heater within the cavity.

5. The aerosol-generating system according to claim 1, wherein the at least one second heater conforms to a shape of side walls of the cavity.

6. The aerosol-generating system according to claim 1, wherein the at least one heater is an electrically powered heater comprising at least one electrically resistive track provided on a flexible substrate.

7. The aerosol-generating system according to claim 1, wherein a longitudinal length of the recess is at least about 50% of a longitudinal length of the at least one side wall.

8. The aerosol-generating system according to claim 1, wherein the base is substantially circular, and the recess has a substantially circular cross-section, a ratio of a radius of the base to a radius of the recess at the base being between about 1.5 and about 4.0.

9. The aerosol-generating system according to claim 1, wherein the recess has a frusto-conical shape, and a substantially circular cross-section.

10. The aerosol-generating system according to claim 1, wherein a longitudinal length of the at least one side wall is at least 2 times a radius of the base.

11. The aerosol-generating system according to claim 1, wherein the capsule is filled with the aerosol-forming substrate to reach a level between about 90% and about 110% of a longitudinal length of the recess.

12. The aerosol-generating system according to claim 1, wherein the aerosol-forming substrate comprises nicotine and at least one aerosol-former.

* * * * *